United States Patent
Poppe et al.

(10) Patent No.: US 11,633,569 B2
(45) Date of Patent: Apr. 25, 2023

(54) MOTORIZED TELESCOPING MEDICAL DEVICE DELIVERY SYSTEM

(71) Applicant: BOSTON SCIENTIFIC SCIMED, INC., Maple Grove, MN (US)

(72) Inventors: Kevin Robert Poppe, New Brighton, MN (US); Daniel J. Foster, Lino Lakes, MN (US); Christopher Jay Scheff, Elk River, MN (US); Bradley S. Swehla, Eagan, MN (US); Peter James Keogh, Dublin (IE); Stephen J. Burke, Tipperary (IE); Michael J. Kane, Saint Paul, MN (US)

(73) Assignee: Boston Scientific Scimed, Inc., Maple Grove, MN (US)

(*) Notice: Subject to any disclaimer, the term of this patent is extended or adjusted under 35 U.S.C. 154(b) by 1025 days.

(21) Appl. No.: 16/396,236

(22) Filed: Apr. 26, 2019

(65) Prior Publication Data

US 2019/0329002 A1     Oct. 31, 2019

Related U.S. Application Data

(60) Provisional application No. 62/662,873, filed on Apr. 26, 2018.

(51) Int. Cl.
*A61M 25/01* (2006.01)
*A61F 2/24* (2006.01)
(Continued)

(52) U.S. Cl.
CPC ........... *A61M 25/01* (2013.01); *A61F 2/2436* (2013.01); *A61F 2/966* (2013.01); *A61M 25/005* (2013.01);
(Continued)

(58) Field of Classification Search
CPC ............ A61M 25/003; A61M 25/0014; A61M 2025/0175; A61M 25/01; A61M 25/0026;
(Continued)

(56) References Cited

U.S. PATENT DOCUMENTS 3,674,014 A    7/1972  Tillander
4,798,598 A    1/1989  Bonello et al.
(Continued)

FOREIGN PATENT DOCUMENTS

EP    0778040 A2    6/1997
EP    1011520 A1    6/2000
(Continued)

OTHER PUBLICATIONS

International Search Report and Written Opinion dated Jun. 27, 2019 for International Application No. PCT/US2019/029349.
(Continued)

*Primary Examiner* — Kathleen S Holwerda
*Assistant Examiner* — Lauren Dubose
(74) *Attorney, Agent, or Firm* — Seager, Tufte & Wickhem LLP

(57) ABSTRACT

A system for delivering an implantable medical device includes a handle housing. An outer sheath is coupler secured to a proximal end of an outer sheath that is configured to cover at least a portion of the implantable medical device. An outer sheath drive assembly is operably coupled to the outer sheath coupler and is configured to translate the outer sheath relative to the handle housing. An actuation shaft coupler is secured to a proximal end of an activation shaft. An actuation shaft drive assembly is operably coupled to the actuation shaft coupler and is configured to cause the actuation shaft to translate relative to the handle housing and shift the implantable medical device from a first position and
(Continued)

a second position in which the implantable medical device is radially expanded relative to the first position.

18 Claims, 10 Drawing Sheets

(51) Int. Cl.
  *A61F 2/966* (2013.01)
  *A61M 25/00* (2006.01)
  *A61B 17/00* (2006.01)
  *A61F 2/95* (2013.01)

(52) U.S. Cl.
  CPC ............... *A61M 25/0026* (2013.01); *A61B 2017/00526* (2013.01); *A61F 2/2466* (2013.01); *A61F 2/9517* (2020.05); *A61M 2025/0175* (2013.01)

(58) Field of Classification Search
  CPC ....... A61M 25/005; A61F 2/966; A61F 2/962; A61F 2/2436; A61F 2/2466; A61F 2/9517; A61F 2/95–2/97; A61F 2/2427–2/2439
  See application file for complete search history.

(56) References Cited

U.S. PATENT DOCUMENTS

| | | | |
|---|---|---|---|
| 4,923,462 A * | 5/1990 | Stevens .......... | A61B 17/320758 606/159 |
| 4,955,384 A | 9/1990 | Taylor et al. | |
| 4,985,022 A | 1/1991 | Fearnot et al. | |
| 4,998,923 A | 3/1991 | Samson et al. | |
| 5,003,989 A | 4/1991 | Taylor et al. | |
| 5,095,915 A | 3/1992 | Engelson | |
| 5,315,996 A | 5/1994 | Lundquist | |
| 5,406,960 A | 4/1995 | Corso, Jr. | |
| 5,437,288 A | 8/1995 | Schwartz et al. | |
| 5,570,701 A | 11/1996 | Ellis et al. | |
| 5,599,492 A | 2/1997 | Engelson | |
| 5,746,701 A | 5/1998 | Noone | |
| 5,749,837 A | 5/1998 | Palermo et al. | |
| 5,769,796 A | 6/1998 | Palermo et al. | |
| 5,772,609 A | 6/1998 | Nguyen et al. | |
| 5,776,080 A | 7/1998 | Thome et al. | |
| 5,833,632 A | 11/1998 | Jacobsen et al. | |
| 5,902,254 A | 5/1999 | Magram | |
| 5,931,830 A | 8/1999 | Jacobsen et al. | |
| 5,951,494 A | 9/1999 | Wang et al. | |
| 6,001,068 A | 12/1999 | Uchino et al. | |
| 6,017,319 A | 1/2000 | Jacobsen et al. | |
| 6,139,510 A | 10/2000 | Palermo | |
| 6,273,876 B1 | 8/2001 | Klima et al. | |
| 6,606,921 B2 | 8/2003 | Noetzold | |
| 6,739,787 B1 | 5/2004 | Bystrom | |
| 6,918,882 B2 | 7/2005 | Skujins et al. | |
| 6,921,397 B2 | 7/2005 | Corcoran et al. | |
| 7,055,656 B2 | 6/2006 | Drew | |
| 7,074,197 B2 | 7/2006 | Reynolds et al. | |
| 7,338,495 B2 | 3/2008 | Adams | |
| 7,413,563 B2 | 8/2008 | Corcoran et al. | |
| 7,533,906 B2 | 5/2009 | Luettgen et al. | |
| 7,540,865 B2 | 6/2009 | Griffin et al. | |
| 7,579,550 B2 | 8/2009 | Dayton et al. | |
| 7,618,379 B2 | 11/2009 | Reynolds et al. | |
| 7,625,364 B2 | 12/2009 | Corcoran et al. | |
| 7,780,611 B2 | 8/2010 | Griego et al. | |
| 7,784,376 B2 | 8/2010 | Wen | |
| 7,824,345 B2 | 11/2010 | Euteneuer et al. | |
| 7,841,994 B2 | 11/2010 | Skujins et al. | |
| 7,850,623 B2 | 12/2010 | Griffin et al. | |
| 7,854,109 B2 | 12/2010 | Zubiate et al. | |
| 7,914,466 B2 | 3/2011 | Davis et al. | |
| 7,914,467 B2 | 3/2011 | Layman et al. | |
| 7,918,080 B2 | 4/2011 | Zubiate et al. | |
| 7,993,286 B2 | 8/2011 | Reynolds et al. | |
| 8,022,331 B2 | 9/2011 | Reynolds et al. | |
| 8,047,236 B2 | 11/2011 | Perry | |
| 8,048,004 B2 | 11/2011 | Davis et al. | |
| 8,048,060 B2 | 11/2011 | Griffin et al. | |
| 8,099,939 B2 | 1/2012 | Zubiate et al. | |
| 8,100,031 B2 | 1/2012 | Zubiate et al. | |
| 8,105,246 B2 | 1/2012 | Voeller et al. | |
| 8,124,876 B2 | 2/2012 | Dayton et al. | |
| 8,137,293 B2 | 3/2012 | Zhou et al. | |
| 8,157,751 B2 | 4/2012 | Adams et al. | |
| 8,182,465 B2 | 5/2012 | Griffin et al. | |
| 8,192,422 B2 | 6/2012 | Zubiate et al. | |
| 8,197,419 B2 | 6/2012 | Field et al. | |
| 8,231,551 B2 | 7/2012 | Griffin et al. | |
| 8,257,279 B2 | 9/2012 | Davis et al. | |
| 8,292,829 B2 | 10/2012 | Griego et al. | |
| 8,317,777 B2 | 11/2012 | Zubiate et al. | |
| 8,376,865 B2 | 2/2013 | Forster et al. | |
| 8,376,961 B2 | 2/2013 | Layman et al. | |
| 8,377,035 B2 | 2/2013 | Zhou et al. | |
| 8,397,481 B2 | 3/2013 | Zubiate et al. | |
| 8,409,114 B2 | 4/2013 | Parins | |
| 8,414,506 B2 | 4/2013 | Reynolds et al. | |
| 8,425,408 B2 | 4/2013 | Boulais et al. | |
| 8,443,692 B2 | 5/2013 | Zubiate et al. | |
| 8,449,526 B2 | 5/2013 | Snyder et al. | |
| 8,459,138 B2 | 6/2013 | Zubiate et al. | |
| 8,475,366 B2 | 7/2013 | Boulais et al. | |
| 8,485,992 B2 | 7/2013 | Griffin et al. | |
| 8,535,219 B2 | 9/2013 | Smith et al. | |
| 8,535,243 B2 | 9/2013 | Shireman | |
| 8,551,020 B2 | 10/2013 | Chen et al. | |
| 8,551,021 B2 | 10/2013 | Voeller et al. | |
| 8,556,914 B2 | 10/2013 | Vrba | |
| 8,608,648 B2 | 12/2013 | Banik et al. | |
| 8,622,894 B2 | 1/2014 | Banik et al. | |
| 8,636,716 B2 | 1/2014 | Griffin et al. | |
| 8,656,697 B2 | 2/2014 | Zubiate et al. | |
| 8,677,602 B2 | 3/2014 | Dayton et al. | |
| 8,758,268 B2 | 6/2014 | Bown et al. | |
| 8,784,337 B2 | 7/2014 | Voeller et al. | |
| 8,795,202 B2 | 8/2014 | Northrop et al. | |
| 8,795,254 B2 | 8/2014 | Layman et al. | |
| 8,821,477 B2 | 9/2014 | Northrop et al. | |
| 8,833,197 B2 | 9/2014 | Zubiate et al. | |
| 8,845,552 B2 | 9/2014 | Griego et al. | |
| 8,864,654 B2 | 10/2014 | Kleiner et al. | |
| 8,870,790 B2 | 10/2014 | Davis et al. | |
| 8,900,163 B2 | 12/2014 | Jacobsen et al. | |
| 8,915,865 B2 | 12/2014 | Jacobsen et al. | |
| 8,932,235 B2 | 1/2015 | Jacobsen et al. | |
| 8,936,558 B2 | 1/2015 | Jacobsen et al. | |
| 8,939,916 B2 | 1/2015 | Jacobsen et al. | |
| 8,945,096 B2 | 2/2015 | Zubiate et al. | |
| 9,005,114 B2 | 4/2015 | Zubiate et al. | |
| 9,011,318 B2 | 4/2015 | Choset et al. | |
| 9,023,011 B2 | 5/2015 | Griffin et al. | |
| 9,072,874 B2 | 7/2015 | Northrop et al. | |
| 9,370,432 B2 | 6/2016 | Bennett et al. | |
| 9,375,234 B2 | 6/2016 | Vrba | |
| 9,386,911 B2 | 7/2016 | Zubiate et al. | |
| 9,387,308 B2 | 7/2016 | Hinchliffe et al. | |
| 9,387,309 B2 | 7/2016 | Parodi et al. | |
| 9,402,682 B2 | 8/2016 | Worrell et al. | |
| 2001/0037141 A1 | 11/2001 | Yee et al. | |
| 2003/0069520 A1 | 4/2003 | Skujins et al. | |
| 2003/0069521 A1 | 4/2003 | Reynolds et al. | |
| 2004/0220499 A1 | 11/2004 | Griego et al. | |
| 2004/0243143 A1 | 12/2004 | Corcoran et al. | |
| 2005/0080400 A1 | 4/2005 | Corcoran et al. | |
| 2005/0090848 A1 | 4/2005 | Adams | |
| 2005/0267444 A1 | 12/2005 | Griffin et al. | |
| 2006/0111615 A1 | 5/2006 | Danitz et al. | |
| 2006/0122537 A1 | 6/2006 | Reynolds et al. | |
| 2006/0179966 A1 | 8/2006 | Kuo | |
| 2006/0189896 A1 | 8/2006 | Davis et al. | |
| 2007/0049902 A1 | 3/2007 | Griffin et al. | |

(56) References Cited

U.S. PATENT DOCUMENTS

| | | |
|---|---|---|
| 2007/0066900 A1 | 3/2007 | O'Keeffe |
| 2007/0083132 A1 | 4/2007 | Sharrow |
| 2007/0100285 A1 | 5/2007 | Griffin et al. |
| 2007/0114211 A1 | 5/2007 | Reynolds et al. |
| 2007/0135734 A1 | 6/2007 | Reynolds et al. |
| 2007/0233043 A1 | 10/2007 | Dayton et al. |
| 2007/0244414 A1 | 10/2007 | Reynolds et al. |
| 2008/0064989 A1 | 3/2008 | Chen et al. |
| 2008/0077119 A1 | 3/2008 | Snyder et al. |
| 2008/0194994 A1 | 8/2008 | Bown et al. |
| 2008/0205980 A1 | 8/2008 | Zubiate et al. |
| 2008/0245173 A1 | 10/2008 | Schwerin et al. |
| 2008/0262474 A1 | 10/2008 | Northrop |
| 2009/0036833 A1 | 2/2009 | Parins |
| 2009/0043228 A1 | 2/2009 | Northrop et al. |
| 2009/0043283 A1 | 2/2009 | Turnlund et al. |
| 2009/0099638 A1* | 4/2009 | Grewe ................ A61F 2/9662 623/1.11 |
| 2009/0143768 A1 | 6/2009 | Parodi et al. |
| 2009/0156999 A1 | 6/2009 | Adams et al. |
| 2009/0171151 A1 | 7/2009 | Choset et al. |
| 2009/0312606 A1 | 12/2009 | Dayton et al. |
| 2010/0063480 A1 | 3/2010 | Shireman |
| 2010/0076266 A1 | 3/2010 | Boulais et al. |
| 2010/0080892 A1 | 4/2010 | O'Brien et al. |
| 2010/0145308 A1 | 6/2010 | Layman et al. |
| 2010/0249655 A1 | 9/2010 | Lemon |
| 2010/0286566 A1 | 11/2010 | Griffin et al. |
| 2010/0294071 A1 | 11/2010 | Zubiate et al. |
| 2010/0305475 A1 | 12/2010 | Hinchliffe et al. |
| 2011/0056320 A1 | 3/2011 | Zubiate et al. |
| 2011/0082443 A1 | 4/2011 | Griffin et al. |
| 2011/0152613 A1 | 6/2011 | Zubiate et al. |
| 2011/0178588 A1* | 7/2011 | Haselby ................ A61F 2/9661 623/1.11 |
| 2011/0184241 A1 | 7/2011 | Zubiate et al. |
| 2011/0257478 A1 | 10/2011 | Kleiner et al. |
| 2011/0264191 A1 | 10/2011 | Rothstein |
| 2012/0160537 A1 | 6/2012 | Wen |
| 2013/0123796 A1 | 5/2013 | Sutton et al. |
| 2013/0123912 A1 | 5/2013 | Tung et al. |
| 2014/0235361 A1 | 8/2014 | Forster et al. |
| 2015/0305901 A1* | 10/2015 | Headley ................ A61F 2/966 623/1.11 |
| 2016/0100943 A1* | 4/2016 | Liu ........................ A61F 2/2436 623/2.11 |
| 2016/0317301 A1 | 11/2016 | Quadri et al. |
| 2017/0172773 A1* | 6/2017 | Gong ................ A61M 25/0102 |
| 2018/0140323 A1 | 5/2018 | Foster et al. |

FOREIGN PATENT DOCUMENTS

| | | |
|---|---|---|
| EP | 2455128 A2 | 5/2013 |
| JP | 2004514463 A | 5/2004 |
| JP | 2009512497 A | 3/2009 |
| JP | 5575840 B2 | 8/2014 |
| WO | 2006041612 A2 | 4/2006 |
| WO | 2006073581 A2 | 7/2006 |
| WO | 2011133486 A1 | 10/2011 |
| WO | 2011137531 A1 | 11/2011 |
| WO | 2016035757 A1 | 3/2016 |

OTHER PUBLICATIONS

International Search Report and Written Opinion dated Mar. 2, 2018 for International Application No. PCT/US2017/062113.
International Search Report and Written Opinion dated May 22, 2018 for International Application No. PCT/US2018/022371.
International Search Report and Written Opinion dated Jun. 15, 2018 for International Application No. PCT/US2018/022377.
International Search Report and Written Opinion dated Aug. 31, 2018 for International Application No. PCT/US2018/030751.

* cited by examiner

MOTORIZED TELESCOPING MEDICAL DEVICE DELIVERY SYSTEM

CROSS-REFERENCE TO RELATED APPLICATIONS

This application claims the benefit of priority under 35 U.S.C. § 119 to U.S. Provisional Application Ser. No. 62/662,873, filed Apr. 26, 2018, the entirety of which is incorporated herein by reference.

TECHNICAL FIELD

The present disclosure pertains to medical device delivery systems. More particularly, the present disclosure pertains to medical device delivery systems that include one or more motors actuating a telescoping assembly to deliver and deploy a medical device.

BACKGROUND

A wide variety of intracorporeal medical devices have been developed for medical use, for example, intravascular use. Some of these devices include guidewires, catheters, and the like. These devices are manufactured by any one of a variety of different manufacturing methods and may be used according to any one of a variety of methods. Of the known medical devices and methods, each has certain advantages and disadvantages. There is an ongoing need to provide alternative medical devices as well as alternative methods for manufacturing and using medical devices.

SUMMARY

This disclosure provides design, material, manufacturing method, and use alternatives for medical devices. An example system for delivering an implantable medical device includes a handle housing. An outer sheath coupler is secured to a proximal end of an outer sheath that is configured to cover at least a portion of the implantable medical device. An outer sheath drive assembly is operably coupled to the outer sheath coupler and is configured to translate the outer sheath relative to the handle housing. An actuation shaft coupler is secured to a proximal end of an actuation shaft, the actuation shaft extending within the outer sheath. An actuation shaft drive assembly is operably coupled to the actuation shaft coupler and is configured to cause the actuation shaft to translate relative to the handle housing and shift the implantable medical device between a first position and a second position in which the implantable medical device is radially expanded relative to the first position.

Alternatively or additionally, the outer sheath drive assembly may further include an outer sheath drive assembly motor having a motor coupling, an outer sheath drive assembly threaded rod operably coupled to the motor coupling such that actuation of the outer sheath drive assembly motor causes the outer sheath drive assembly threaded rod to rotate and an outer sheath nut threadedly engaged with the outer sheath drive assembly threaded rod and held against rotation such that rotation of the outer sheath drive assembly threaded rod causes the outer sheath nut to translate relative to the outer sheath drive assembly threaded rod. The outer sheath nut may be configured to engage the outer sheath coupler such that translation of the outer sheath nut relative to the outer sheath drive assembly threaded rod causes the outer sheath to translate relative to the handle housing.

Alternatively or additionally, the outer sheath drive assembly may further include a thrust bearing configured to secure the outer sheath drive assembly threaded rod at an end away from the outer sheath drive assembly motor while permitting the outer sheath drive assembly threaded rod to rotate relative to the thrust bearing.

Alternatively or additionally, the outer sheath drive nut may be held against rotation by virtue of being engaged with the outer sheath coupler.

Alternatively or additionally, the outer sheath drive assembly motor may include a direct drive motor.

Alternatively or additionally, the outer sheath drive assembly motor may further include a gearbox.

Alternatively or additionally, the actuation shaft drive assembly may include an actuation shaft drive assembly motor having a motor coupling, an actuation shaft drive assembly threaded rod operably coupled to the motor coupling such that actuation of the actuation shaft drive assembly motor causes the actuation shaft drive assembly threaded rod to rotate and an actuation shaft nut threadedly engaged with the actuation shaft drive assembly threaded rod and held against rotation such that rotation of the actuation shaft drive assembly threaded rod causes the outer sheath nut to translate relative to the actuation shaft drive assembly threaded rod. The actuation shaft nut may be configured to engage the actuation shaft coupler such that translation of the actuation shaft nut relative to the actuation shaft drive assembly threaded rod causes the outer sheath to translate relative to the handle housing.

Alternatively or additionally, the actuation shaft drive assembly may further include a thrust bearing configured to secure the actuation shaft drive assembly threaded rod at an end away from the actuation shaft drive assembly motor while permitting the actuation shaft drive assembly threaded rod to rotate relative to the thrust bearing.

Alternatively or additionally, the actuation shaft drive nut may be held against rotation by virtue of being engaged with the activation shaft coupler.

Alternatively or additionally, the actuation shaft coupler may be disposed within the handle housing at a position that is proximal of the outer sheath coupler.

Alternatively or additionally, the system may further include a controller disposed within the handle housing and configured to control operation of the outer sheath drive assembly and/or the actuation shaft drive assembly.

Alternatively or additionally, the controller may be further configured to receive feedback from the outer sheath drive assembly and/or the activation shaft drive assembly.

Alternatively or additionally, the system may further include a power supply disposed within the handle and operably coupled to the controller.

Another example system for delivering an implantable medical device includes a handle housing and an outer sheath that is configured to cover at least a portion of the implantable medical device. An outer sheath coupler is secured to the outer sheath such that translation of the outer sheath coupler relative to the handle housing causes translation of the outer sheath relative to the handle housing. An outer sheath nut is threadedly disposed on a first threaded rod and is operably coupled to the outer sheath coupler. An outer sheath drive motor is operably coupled to the outer sheath nut such that actuation of the outer sheath drive motor causes the outer sheath nut to translate relative to the first threaded rod and thus causes the outer sheath coupler to translate relative to the handle housing. An actuation shaft extends within the outer sheath and is operably coupled to translation members secured relative to the implantable medical device such that translation of the actuation shaft causes translation of the translation members which in turn causes the implantable medical device to shift from a delivery configuration to a deployment configuration. An actuation shaft coupler is secured to the actuation shaft such that translation of the actuation shaft coupler relative to the handle housing causes translation of the actuation shaft relative to the handle housing. An actuation shaft nut is threadedly disposed on a second threaded rod and operably coupled to the actuation shaft coupler. An actuation shaft drive motor is operably coupled to the actuation shaft nut such that actuation of the actuation shaft drive motor causes the actuation shaft nut to translate relative to the second threaded rod and thus causes the actuation shaft coupler to translate relative to the handle housing.

Alternatively or additionally, the system may further include a first thrust bearing configured to secure the first threaded rod at an end away from the outer sheath drive motor while permitting the first threaded rod to rotate relative to the first thrust bearing.

Alternatively or additionally, the system may further include a second thrust bearing configured to secure the second threaded rod at an end away from the activation shaft drive motor while permitting the second threaded rod to rotate relative to the second thrust bearing.

Alternatively or additionally, the outer sheath nut may have an overall length of about 12 mm to about 150 mm.

Alternatively or additionally, the actuation shaft nut may have an overall length of about 12 mm to about 150 mm.

Alternatively or additionally, the system may further include a controller disposed within the handle housing and configured to control operation of the outer sheath drive motor and/or the actuation shaft drive motor.

Another example system for delivering an implantable medical device includes a handle housing. An actuation shaft is operably coupled to translation members secured relative to the implantable medical device such that translation of the actuation shaft causes translation of the translation members which in turn causes the implantable medical device to shift from a delivery configuration to a deployment configuration. An actuation shaft coupler is secured to the activation shaft such that translation of the actuation shaft coupler relative to the handle housing causes translation of the actuation shaft relative to the handle housing. An actuation shaft nut is threadedly disposed on a threaded rod and is operably coupled to the actuation shaft coupler. An actuation shaft drive motor is operably coupled to the actuation shaft nut such that actuation of the actuation shaft drive motor causes the actuation shaft nut to translate relative to the second threaded rod and thus causes the actuation shaft coupler to translate relative to the handle housing.

The above summary of some embodiments is not intended to describe each disclosed embodiment or every implementation of the present disclosure. The Figures, and Detailed Description, which follow, more particularly exemplify these embodiments.

BRIEF DESCRIPTION OF THE DRAWINGS

The disclosure may be more completely understood in consideration of the following detailed description in connection with the accompanying drawings, in which.

Figure 1:
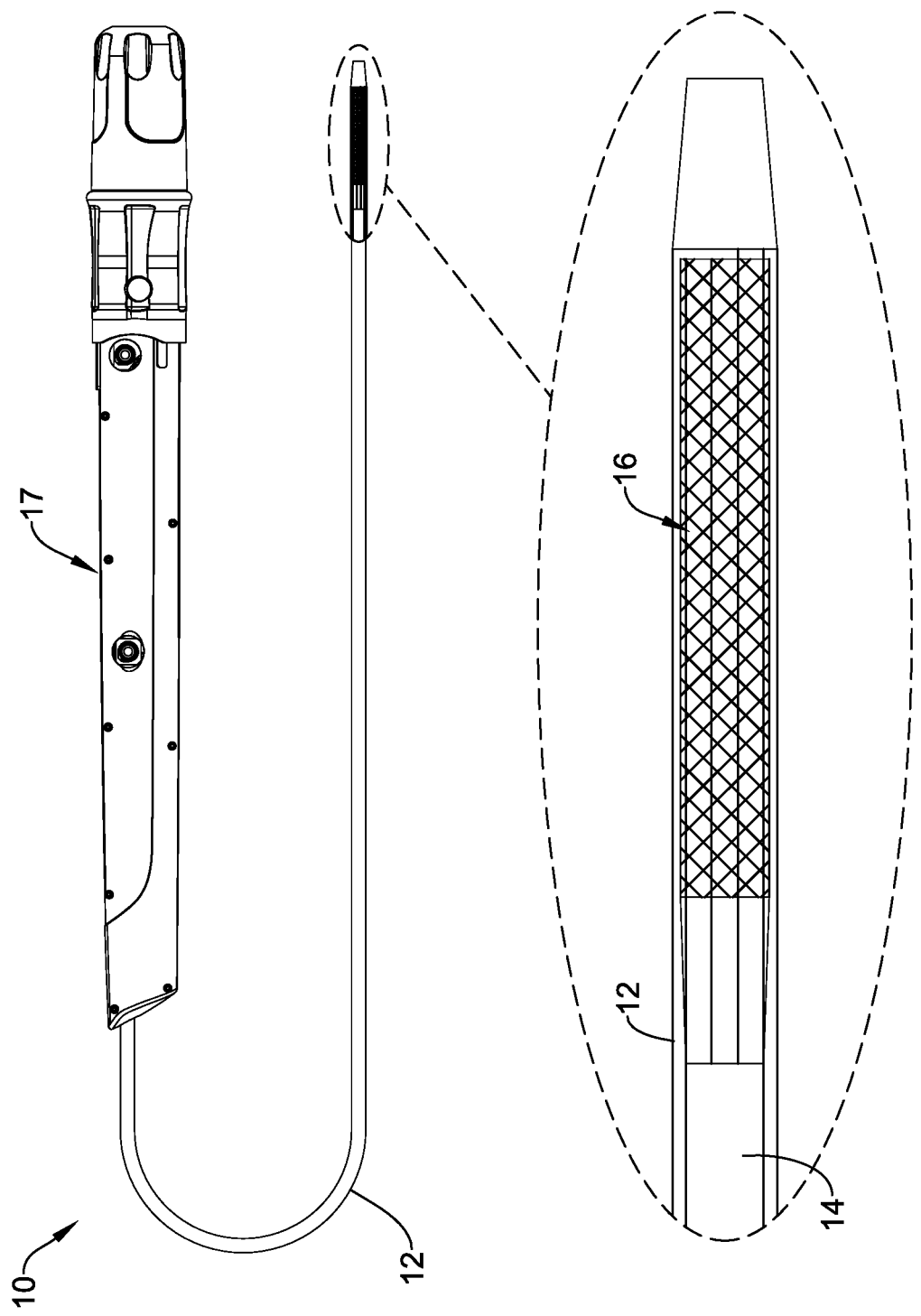
FIG. 1 is a side view of an example medical device system.

While the disclosure is amenable to various modifications and alternative forms, specifics thereof have been shown by way of example in the drawings and will be described in detail. It should be understood, however, that the intention is not to limit the disclosure to the particular embodiments described. On the contrary, the intention is to cover all modifications, equivalents, and alternatives falling within the spirit and scope of the disclosure.

DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (e.g., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include one or more particular features, structures, and/or characteristics. However, such recitations do not necessarily mean that all embodiments include the particular features, structures, and/or characteristics. Additionally, when particular features, structures, and/or characteristics are described in connection with one embodiment, it should be understood that such features, structures, and/or characteristics may also be used connection with other embodiments whether or not explicitly described unless clearly stated to the contrary.

The following detailed description should be read with reference to the drawings in which similar elements in different drawings are numbered the same. The drawings, which are not necessarily to scale, depict illustrative embodiments and are not intended to limit the scope of the invention.

Diseases and/or medical conditions that impact the cardiovascular system are prevalent throughout the world. Traditionally, treatment of the cardiovascular system was often conducted by directly accessing the impacted part of the body. For example, treatment of a blockage in one or more of the coronary arteries was traditionally treated using coronary artery bypass surgery. As can be readily appreciated, such therapies are rather invasive to the patient and require significant recovery times and/or treatments. More recently, less invasive therapies have been developed. For example, therapies have been developed which allow a blocked coronary artery to be accessed and treated via a percutaneous catheter (e.g., angioplasty). Such therapies have gained wide acceptance among patients and clinicians.

Some relatively common medical conditions may include or be the result of inefficiency, ineffectiveness, or complete failure of one or more of the valves within the heart. For example, failure of the aortic valve or the mitral valve can have a serious effect on a human and could lead to serious health condition and/or death if not dealt with properly. Treatment of defective heart valves poses other challenges in that the treatment often requires the repair or outright replacement of the defective valve. Such therapies may be highly invasive to the patient. Disclosed herein are medical devices that may be used for delivering a medical device to a portion of the cardiovascular system in order to diagnose, treat, and/or repair the system. At least some of the medical devices disclosed herein may be used to deliver and implant a replacement heart valve (e.g., a replacement aortic valve, replacement mitral valve, etc.). In addition, the devices disclosed herein may deliver the replacement heart valve percutaneously and, thus, may be much less invasive to the patient. The devices disclosed herein may also provide a number of additional desirable features and benefits as described in more detail below.

The figures illustrate selected components and/or arrangements of a medical device system 10, shown schematically in FIG. 1 for example. It should be noted that in any given figure, some features of the medical device system 10 may not be shown, or may be shown schematically, for simplicity. Additional details regarding some of the components of the medical device system 10 may be illustrated in other figures in greater detail. A medical device system 10 may be used to deliver and/or deploy a variety of medical devices to a number of locations within the anatomy. In at least some embodiments, the medical device system 10 may include a replacement heart valve delivery system (e.g., a replacement aortic valve delivery system) that can be used for percutaneous delivery of a medical implant 16 (shown in the detailed view of FIG. 1), such as a replacement/prosthetic heart valve. This, however, is not intended to be limiting as the medical device system 10 may also be used for other interventions including valve repair, valvuloplasty, delivery of an implantable medical device (e.g., such as a stent, graft, etc.), and the like, or other similar interventions.

The medical device system 10 may generally be described as a catheter system that includes an outer sheath 12, an inner catheter 14 extending at least partially through a lumen of the outer sheath 12, and a medical implant 16 (e.g., a replacement heart valve implant) which may be coupled to the inner catheter 14 and disposed within a lumen of the outer sheath 12 during delivery of the medical implant 16. In some embodiments, a medical device handle 17 may be disposed at a proximal end of the outer sheath 12 and/or the inner catheter 14 and may include one or more actuation mechanisms associated therewith. In other words, one or more tubular members (e.g., the outer sheath 12, the inner catheter 14, etc.) may extend distally from the medical device handle 17. In general, the medical device handle 17 may be designed to manipulate the position of the outer sheath 12 relative to the inner catheter 14 and/or aid in the deployment of the medical implant 16.

In use, the medical device system 10 may be advanced percutaneously through the vasculature to a position adjacent to an area of interest and/or a treatment location. For example, in some embodiments, the medical device system 10 may be advanced through the vasculature to a position adjacent to a defective native valve (e.g., aortic valve, mitral valve, etc.). Alternative approaches to treat a defective aortic valve and/or other heart valve(s) are also contemplated with the medical device system 10. During delivery, the medical implant 16 may be generally disposed in an elongated and low profile "delivery" configuration within the lumen and/or a distal end of the outer sheath 12, as seen schematically in FIG. 1, for example. Once positioned, the outer sheath 12 may be retracted relative to the medical implant 16 and/or the inner catheter 14 to expose the medical implant 16. In some instances, the medical implant 16 may be self-expanding such that exposure of the medical implant 16 may deploy the medical implant 16. Alternatively, the medical implant 16 may be expanded/deployed using the medical device handle 17 in order to translate the medical implant 16 into a generally shortened and larger profile "deployed" configuration suitable for implantation within the anatomy. When the medical implant 16 is suitably deployed within the anatomy, the medical device system 10 may be disconnected, detached, and/or released from the medical implant 16 and the medical device system 10 can be removed from the vasculature, leaving the medical implant 16 in place in a "released" configuration.

It can be appreciated that during delivery and/or deployment of an implantable medical device (e.g., the medical implant 16), portions of the medical device system (e.g., the medical device system 10) may be required to be advanced through tortuous and/or narrow body lumens. Therefore, it may be desirable to utilize components and design medical delivery systems (e.g., such as the medical device system 10 and/or other medical devices) that reduce the profile of portions of the medical device while maintaining sufficient strength (compressive, torsional, etc.) and flexibility of the system as a whole.

Figure 2:
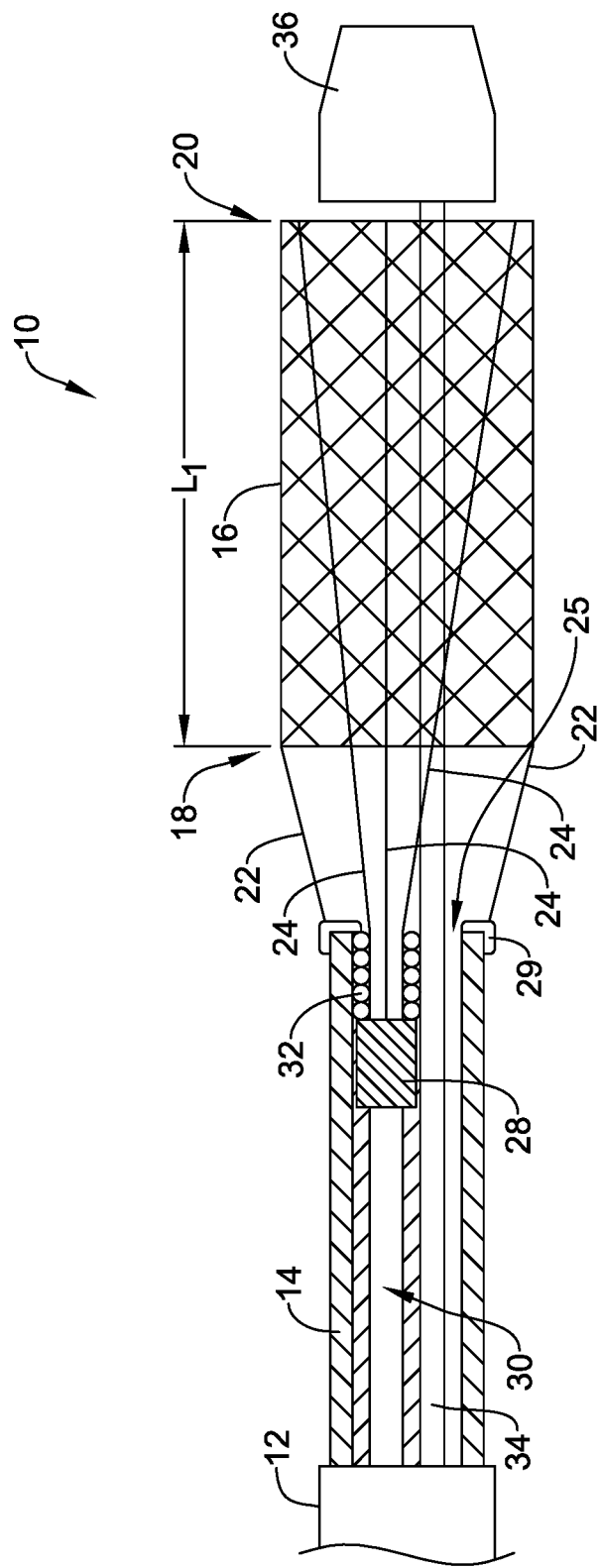
FIG. 2 is a partial cross-sectional view of a portion of an example medical device delivery system.

FIG. 2 illustrates the medical device system 10 in a partially deployed configuration. As illustrated in FIG. 2, the outer sheath 12 of the medical device system 10 has been retracted in a proximal direction to a position proximal of the medical implant 16. In other words, the outer sheath 12 has been retracted (e.g., pulled back) in a proximal direction such that it uncovers the medical device implant 16 from a compact, low-profile delivery position to a partially-deployed position.

In at least some examples contemplated herein, the medical device implant 16 may be designed to self-expand once released from under the outer sheath 12. However, as shown in FIG. 2, the medical device system 10 may be designed such that the implant 16 may be restricted from expanding fully in the radial direction. For example, FIG. 2 shows medical device implant 16 having a partially deployed position denoted as a length "$L_1$."

FIG. 2 further illustrates that in some examples, the implant 16 may include one or more support members 22 coupled to the proximal end 18 of the implant 16. Further, FIG. 2 illustrates that in some examples, the implant 16 may include one or more translation members 24 coupled to the distal end 20 of the implant 16. Additionally, in some examples (such as that illustrated in FIG. 2), the translation members 24 and support members 22 may work together to maintain the implant in a partially-deployed position after the outer sheath 12 has been retracted to uncover the implant 16. For example, FIG. 2 illustrates that the support members 22 may be designed such that the distal end of each of the support members 22 may be coupled to the proximal end of the implant 16 and that the proximal end of each of the support members 22 may be coupled to the distal end of the inner catheter 14. For example, FIG. 2 illustrates that the proximal ends of the support members 22 may be attached to a containment fitting 29 which is rigidly fixed to the distal end of the inner catheter 14. It can be further appreciated that in some instances, the support members 22 may be designed to limit the proximal movement of the proximal end 18 of the implant 16 relative to the distal end of the inner catheter 14.

Additionally, the translation members 24 may be designed to translate in a distal-to-proximal direction such that the translation of the translation members (via operator manipulation at the handle, for example) may "pull" the distal end 20 of the implant closer to the proximal end 18 of the implant 16.

Figure 3:
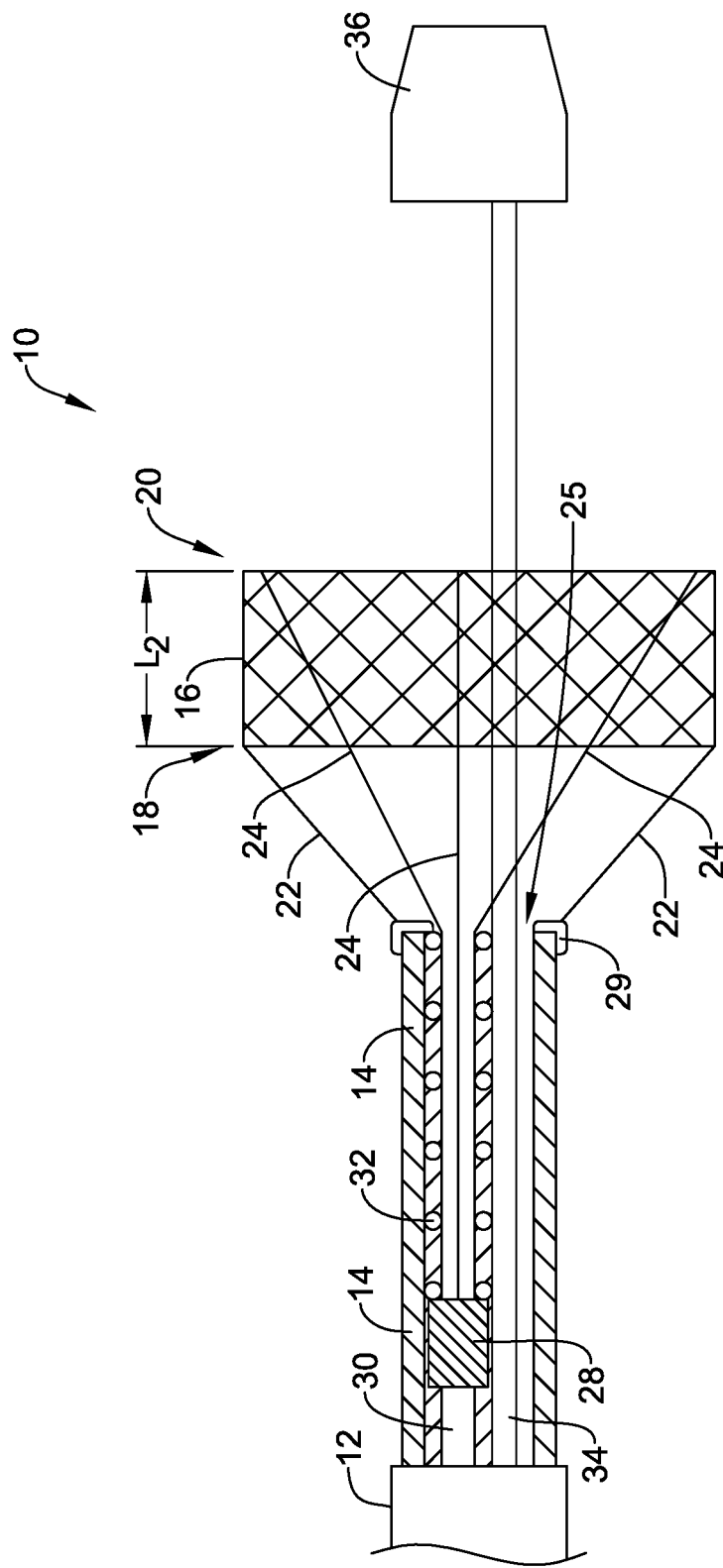
FIG. 3 is a partial cross-sectional view of a portion of an example medical device delivery system.

For example, FIG. 3 illustrates the distal-to-proximal translation of the translation members 24. It can be appreciated that if the support members 22 limit the proximal movement of the proximal end 18 of the implant 16 while the translation members 24 are translated proximally, the implant 16 may both foreshorten (along the longitudinal axis of the implant 16) and also expand radially outward. The foreshortening and radial expansion of implant 16 can be seen by comparing the shape and position of the implant 16 in FIG. 2 to the shape and position of the implant 16 in FIG. 3. The position of the implant 16 shown in FIG. 3 may be described as a fully deployed positioned of the implant 16 (versus the partially deployed positioned of the implant 16 shown in FIG. 2). Further, FIG. 3 depicts the length of the fully deployed implant 16 as "$L_2$", whereby the distance $L_2$ is less than the distance $L_1$ shown in FIG. 2.

Additionally, it can be appreciated that the translation members 24 may be designed to be able extend in a proximal-to-distal direction such that they elongate (e.g., lengthen) the implant 16 (along its longitudinal axis). In other words, the implant 16 may be able to shift between a partially deployed position (shown in FIG. 2) and a fully deployed position (shown in FIG. 3) through the translation (either proximal or distal) of the translation members 24 along the longitudinal axis as the support members 22 limit the movement of the proximal end 18 of the implant 16.

It should be noted that the above description and illustrations regarding the arrangement, attachment features and operation of the support members 22 and the translation members 24 as they engage and function relative to the implant 16 is schematic. It can be appreciated that the design (e.g., arrangement, attachment features, operation, etc.) of the both support member 22 and the translation members 24 as they relate and function relative to the implant 16 may vary. For example, it is possible to design, arrange and operate the translation members 24 and the support members 22 in a variety of ways to achieve the partial and full deployment configurations of the implant 16 described herein.

In some examples, an operator may be able to manipulate the translation members 24 via the handle 17. For example, the handle 17 may include an actuation member designed to control the translation of the translation members 24. FIG. 2 illustrates that the handle member 17 may be coupled to the translation members 24 via an actuation shaft 30 and a coupling member 28. Additionally, FIG. 2 further illustrates that a distal end of actuation shaft 30 may be coupled to the proximal end of the coupling member 28. Further, while not shown in FIG. 2, it can be appreciated that the actuation shaft 30 may extend within the entire length of the inner catheter 14 from the coupling member 28 to the handle member 17.

For purposes of discussion herein, the inner catheter 14 may also be referred to as an inner member or liner 14. The liner 14 may include a number of different features shown in the figures described herein. For example, the liner 14 may include a lumen 25. Further, the translation members 24, coupler 28, actuation shaft 30, tubular guidewire member 34 (described below), and grouping coil 32 (described below) may be disposed within the lumen 25. These are just examples. The inner liner 14 may vary in form. For example, the inner liner 14 may include a single lumen, multiple lumens, or lack a lumen.

As described above, FIG. 2 and FIG. 3 illustrate the translation of translation members 24 in a distal-to-proximal direction (which shortens and radially expands the implant 16, as described above). However, FIG. 3 further illustrates that translation of the translation members 24 in a distal-to-proximal direction is accomplished by translation of the actuation shaft 30 and coupling member 28 within the lumen 25 of the inner catheter 14. For example, as the actuation shaft 30 is retracted (e.g., pulled proximally within lumen 25 of the inner catheter 14), it retracts the coupling member 28 proximally, which, in turn, retracts the translation members 24 in a proximal direction.

In some instances it may be desirable to maintain translation members 24 in a substantially linear configuration as they are translated within the lumen 25 of the inner catheter 14. In some examples, therefore, medical device system 10 may include a component designed to limit and/or prevent the translation members 24 from twisting around each other within the lumen 25 of the inner catheter 14. For example, FIG. 2 and FIG. 3 illustrate a grouping coil 32 wound around the translation members 24 such that the grouping coil 32 maintains the translation members 24 in a substantially liner configuration (and thereby limits and/or prevents the translation members 24 from twisting within lumen 25) as the translation members 24 are translated through the lumen 25 of the inner catheter 14.

FIG. 2 and FIG. 3 further illustrate that the proximal end of the grouping coil 32 may be positioned adjacent the distal end of the coupling member 28 and that the distal end of the grouping coil 32 may be positioned adjacent the distal end of the inner catheter 14. In particular, the distal end of the grouping coil 32 may be prevented from extending distally beyond the distal end of the inner catheter 14 by the containment fitting 29. In other words, the distal end of the grouping coil 32 may contact the containment fitting 29.

It can be further appreciated that the grouping coil 32 may be positioned within the lumen 25 of the inner catheter 14 such that the grouping coil 32 may elongate and shorten (e.g., a length of the grouping coil may adjust) within the lumen 25 of the inner catheter 14. For example, as the coupling member 28 is translated in a proximal direction (shown in FIG. 3 as compared to FIG. 2), the grouping coil 32 may elongate while continuing to group and/or contain the translation members 24 in a substantially linear configuration.

FIG. 2 and FIG. 3 further illustrate that the medical device system 10 may include a tubular guidewire member 34 extending within the lumen 25 of the inner catheter 14. The tubular guidewire member 34 may include a lumen which permits a guidewire to extend and translate therein. In other words, the medical device system 10 may be advanced to a target site within a body over a guidewire extending within the lumen of the tubular guidewire member 34. Further, the tubular guidewire member 34 may extend from the handle member 17, through the lumen 25 of the inner member 14, through the implant 16 and terminate at a nosecone 36.

Figure 4:
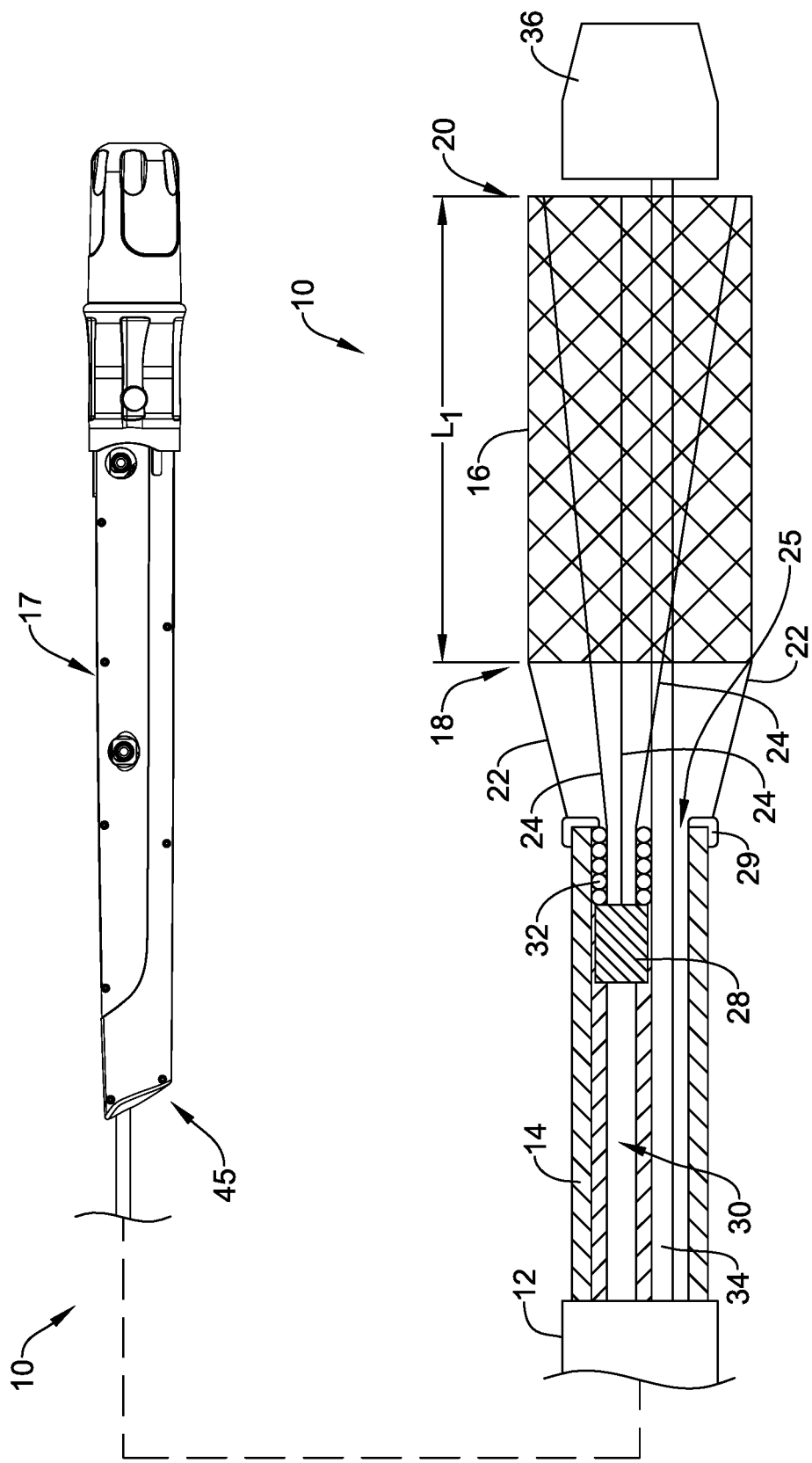
FIG. 4 is a partial cross-sectional view of an example medical device delivery system.

It can be appreciated from the above discussion that the outer member 12, the inner shaft 14, the actuation shaft 30 (which is coupled to the translation members 24) and the tubular guidewire member 34 may all extend from a position adjacent the medical implant 16 to a position in which they enter the handle member 17. For example, FIG. 4 shows that the outer sheath 12, the inner shaft 14, the actuation shaft 30 (which is coupled to the translation members 24) and the tubular guidewire member 34 may extend from an example medical implant 16 (which may be similar in form and function to the medical implant described above) and enter a distal end 45 of the handle member 17.

Figure 5:
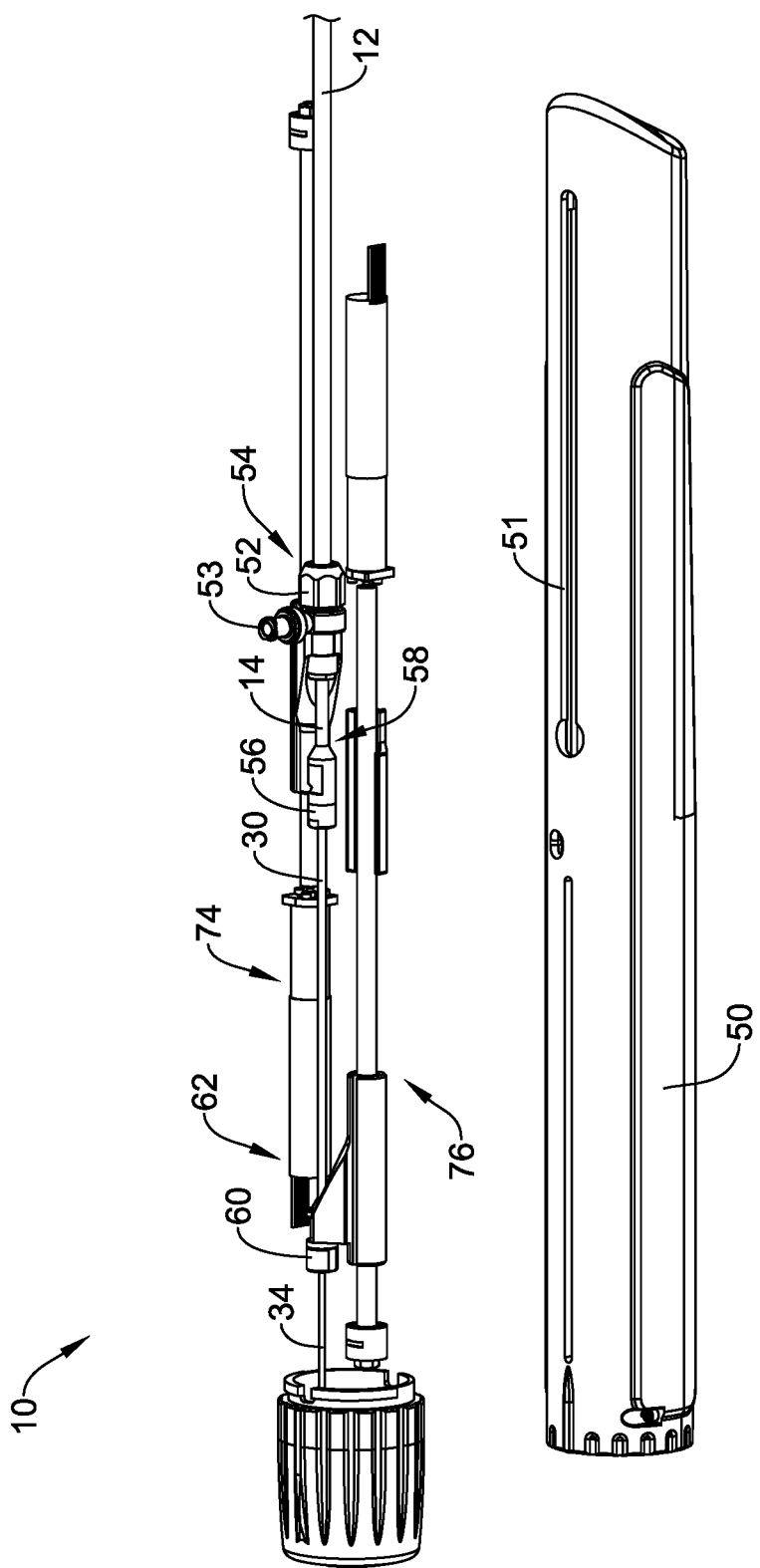
FIG. 5 is an exploded view of an example medical device delivery system.
Figure 6:
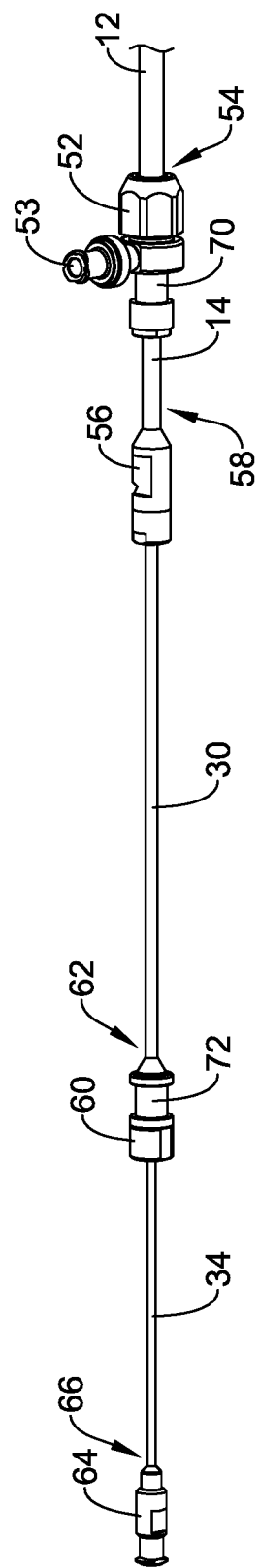
FIG. 6 is a view of a portion of an example medical device delivery system.

FIG. 5 shows the medical device system 10 with a housing portion 50 shown removed to reveal features of the handle 17. FIG. 6 further illustrates the coaxial and telescoping arrangement between the guidewire member 34, the actuation shaft 30, the inner catheter 14 and the outer sheath 12. Within the handle 17, an outer sheath coupler 52 is operably secured to a proximal end 54 of the outer sheath 12 such that the outer sheath 12 moves relative to the handle 17 when the outer sheath coupler 52 moves relative to the housing portion 50. In some cases, the outer sheath coupler 52 may include a luer lock flushing port 53, and the housing portion 50 may include an elongate slot 51 in order to accommodate movement of the outer sheath coupler 52 (and hence movement of the luer lock flushing port 53) relative to the handle 17.

A coupler 56 may be secured to a proximal end 58 of the inner catheter 14. In some cases, the coupler 56 may be fixed in place within the handle 17. An actuation shaft coupler 60 may be operably coupled to a proximal end 62 of the actuation shaft 30 such that the actuation shaft 30 moves relative to the handle 17 when the actuation shaft coupler 60 moves relative to the handle 17. A coupler 64 may be secured to a proximal end 66 of the guidewire member 34. In some cases, the coupler 64 may be fixed in place within the handle 17.

In some cases, as can be seen in FIG. 6, the outer sheath coupler 52 may include an annular recess 70 and the actuation shaft coupler 60 may include an annular recess 72. In some cases, as will be discussed, the annular recess 70 and the annular recess 72 may permit coupling the outer sheath coupler 52 and the actuation shaft coupler 60 with an outer sheath drive assembly 74 and an actuation shaft drive assembly 76, respectively. In some cases, as will be appreciated, the outer sheath drive assembly 74 may be configured to cause the outer sheath coupler 52, and hence the outer sheath 12, to translate relative to the handle 17. The actuation shaft drive assembly 76 may be configured to cause the actuation shaft coupler 60, and hence the actuation shaft 30, to translate relative to the handle 17. The outer sheath drive assembly 74 is better illustrated in FIG. 7 and the actuation shaft drive assembly 76 is better illustrated in FIG. 8.

Figure 7:
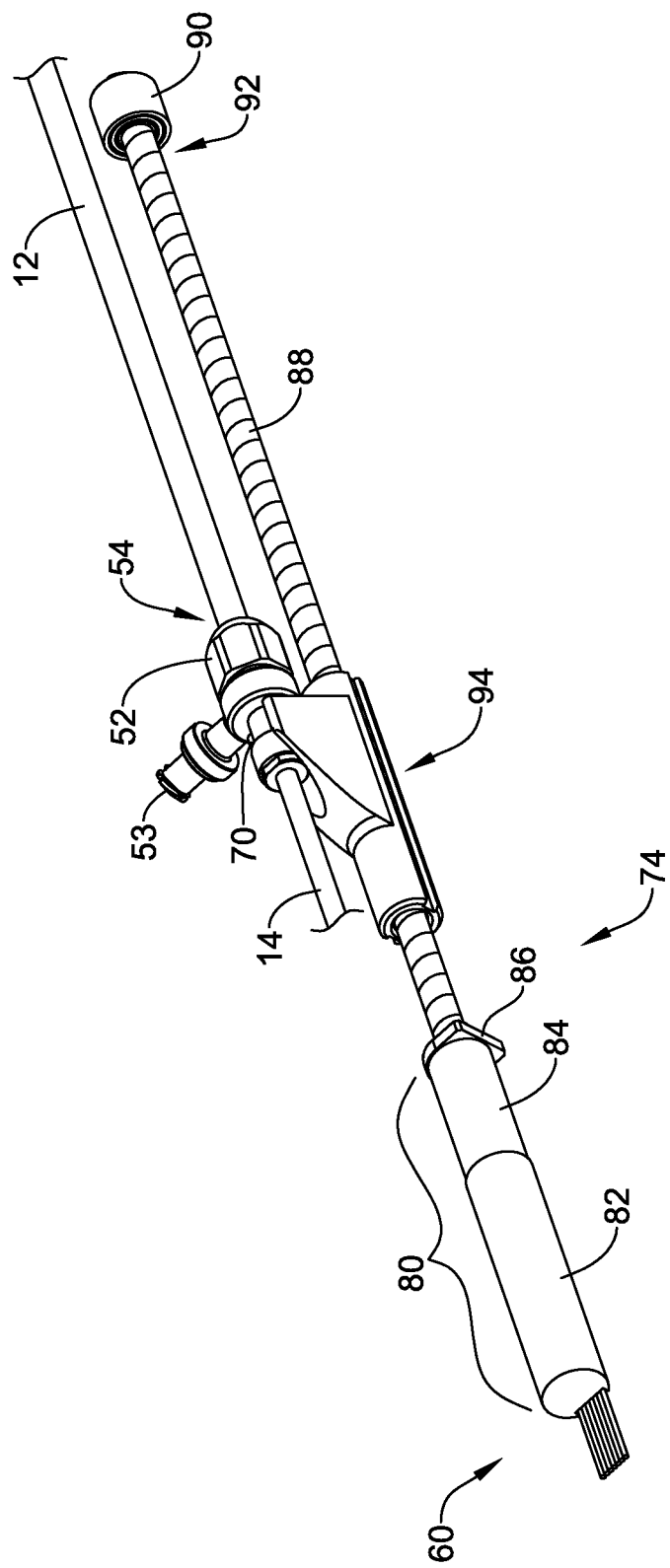
FIG. 7 is a view of a portion of an example medical device delivery system.

As seen in FIG. 7, the outer sheath drive assembly 74 includes an outer sheath drive assembly motor 80. In some cases, the outer sheath drive assembly motor 80 includes a motor 82 and a gear box 84, although in some cases the motor 82 may be a direct drive motor without a separate gear box. In some cases, the outer sheath drive assembly motor 80 includes a motor coupling 86 by which the outer sheath drive assembly motor 80 is operably coupled to an outer sheath drive assembly threaded rod 88. In some instances, the outer sheath drive assembly threaded rod 88 may instead be formed as an integral part of an output shaft of the motor 82. When the outer sheath drive assembly motor 80 is actuated, the outer sheath drive assembly threaded rod 88 is driven into rotation. A thrust bearing 90 accepts a remote end 92 of the outer sheath drive assembly threaded rod 88, and is configured to permit the outer sheath drive assembly threaded rod 88 to rotate relative to the thrust bearing 90. An outer sheath nut 94 is threadedly disposed on the outer sheath drive assembly threaded rod 88 and is held against rotation by virtue of being engaged with the outer sheath coupler 52. As the outer sheath drive assembly threaded rod 88 rotates, the outer sheath nut 94 translates relative to the outer sheath drive assembly threaded rod 88, and as a result, the outer sheath 12 translates relative to the handle 17.

Figure 8:
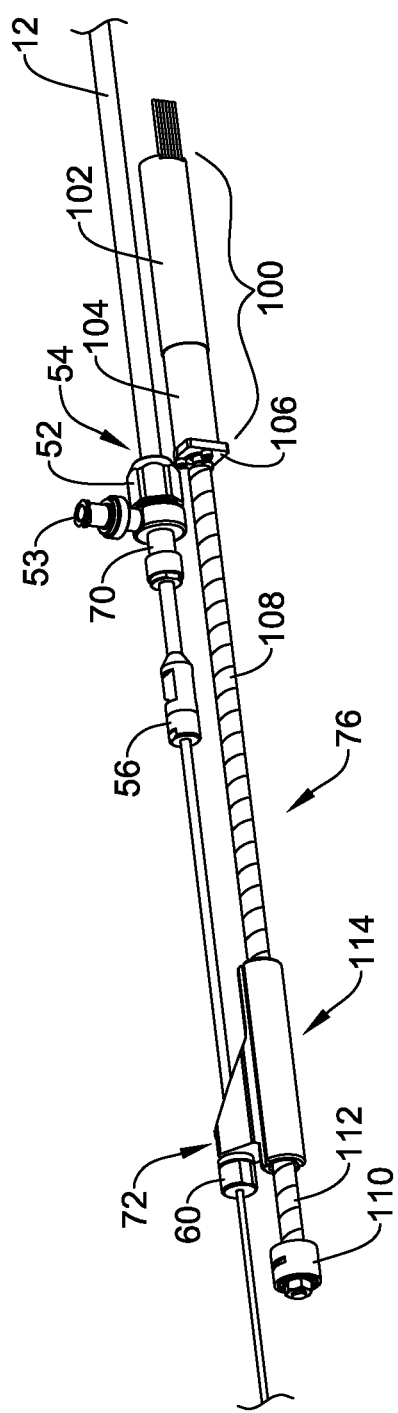
FIG. 8 is a view of a portion of an example medical device delivery system.

As seen in FIG. 8, the actuation shaft drive assembly 76 includes an actuation shaft drive assembly motor 100. In some cases, the actuation shaft drive assembly motor 100 includes a motor 102 and a gear box 104, although in some cases the motor 102 may be a direct drive motor without a separate gear box. In some cases, the actuation shaft drive assembly motor 100 includes a motor coupling 106 by which the actuation shaft drive assembly motor 100 is operably coupled to an actuation shaft drive assembly threaded rod 108. In some instances, the actuation shaft drive assembly threaded rod 108 may instead be formed as an integral part of an output shaft of the motor 102. When the actuation shaft drive assembly motor 100 is actuated, the actuation shaft drive assembly threaded rod 108 is driven into rotation. A thrust bearing 110 accepts a remote end 112 of the actuation shaft drive assembly threaded rod 108, and is configured to permit the actuation shaft drive assembly threaded rod 108 to rotate relative to the thrust bearing 110. An actuation shaft nut 114 is threadedly disposed on the actuation shaft drive assembly threaded rod 108 and is held against rotation by virtue of being engaged with the actuation shaft coupler 60. As the actuation shaft drive assembly threaded rod 108 rotates, the actuation shaft nut 114 translates relative to the actuation shaft drive assembly threaded rod 108, and as a result, the actuation shaft 30 translates relative to the handle 17.

Figure 9:
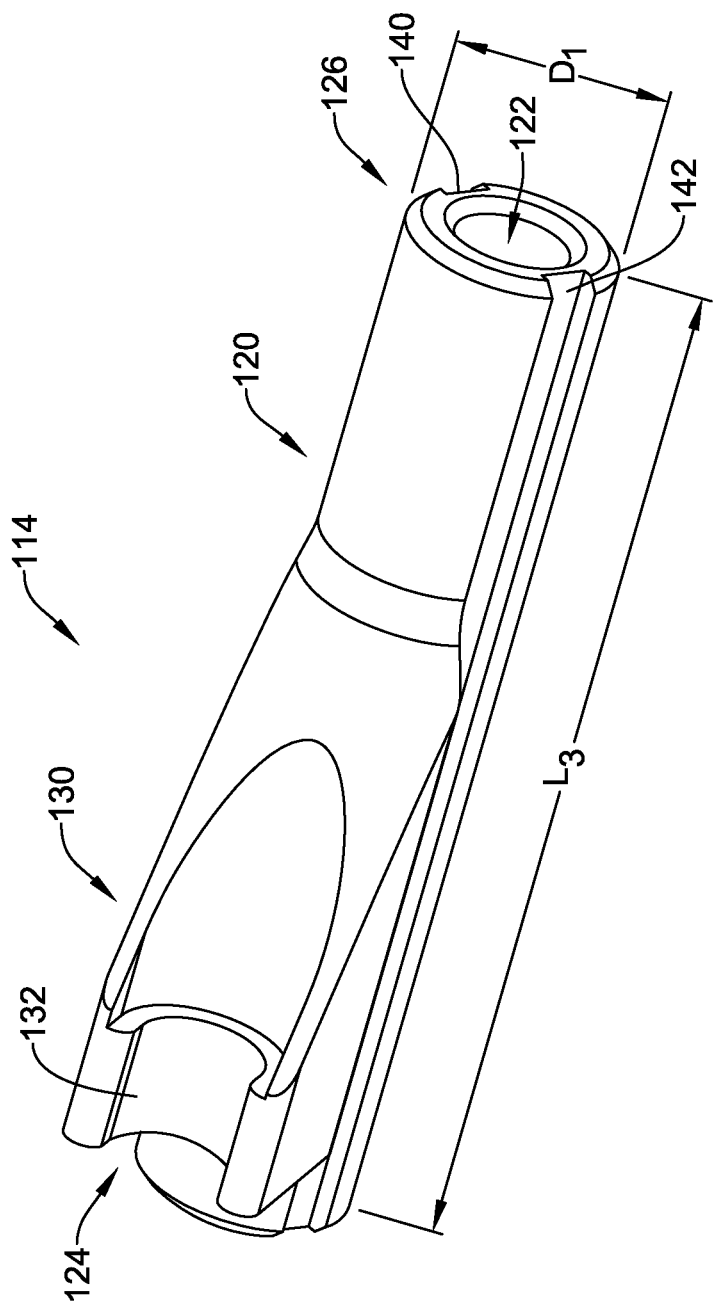
FIG. 9 is a view of a portion of an example medical device delivery system.

FIG. 9 is an enlarged view of the actuation shaft nut 114. In some cases, the outer sheath nut 84 may be of similar construction and configuration. In some instances, the outer sheath nut 84 may have minor differences to accommodate changes in structure of the outer sheath coupler 52. The actuation shaft nut 114 includes a body 120 that defines an aperture 122 that extends through the body 120 from a first end 124 to a second end 126. In some cases, a threaded portion of the aperture 122 may not extend from the first end 124 to the second end 126, but may instead extend over only a portion of the length of the aperture 122. For example, in some cases, about half of the length of the aperture 122 may be threaded. The threaded portion may, for example, be centered within the aperture 122, but this is not required.

In some cases, the body 122 may have an overall length $L_3$ that is larger than a corresponding diameter $D_1$ of the body 122. In some cases, the body 122 may have a length $L_3$ that is in the range of about 12 millimeters (mm) to about 150 mm and a diameter $D_1$ that is in the range of about 3 mm to about 35 mm. In some cases, having a length $L_3$ that is substantially greater than a diameter $D_1$ permits the actuation shaft nut 114 to better handle moments applied to the actuation shaft nut 114. The actuation shaft nut 114 includes a coupler engagement portion 130 that is configured to engage the actuation shaft coupler 60. In some cases, the coupler engagement portion 130 may include an annular portion 132 that is dimensioned to engage the annular recess 72 formed within the actuation shaft coupler 60. In some cases, the actuation shaft nut 114 may include elongate slots 140 and 142 on either side of the body 122. In some cases, the elongate slots 140 and 142 may be used to help locate the actuation shaft nut 114 within the handle 17. In some cases, the elongate slots 140 and 142 may ride along corresponding rails (not illustrated) formed within the handle 17. While two elongate slots 140 and 142 are illustrated, in some cases there may only be a single elongate slot, or there may be three or more elongate slots. In some instances, the elongate slots 140 and 142 riding along the corresponding rails may also help to limit moments applied to the actuation shaft nut 114.

Figure 10:
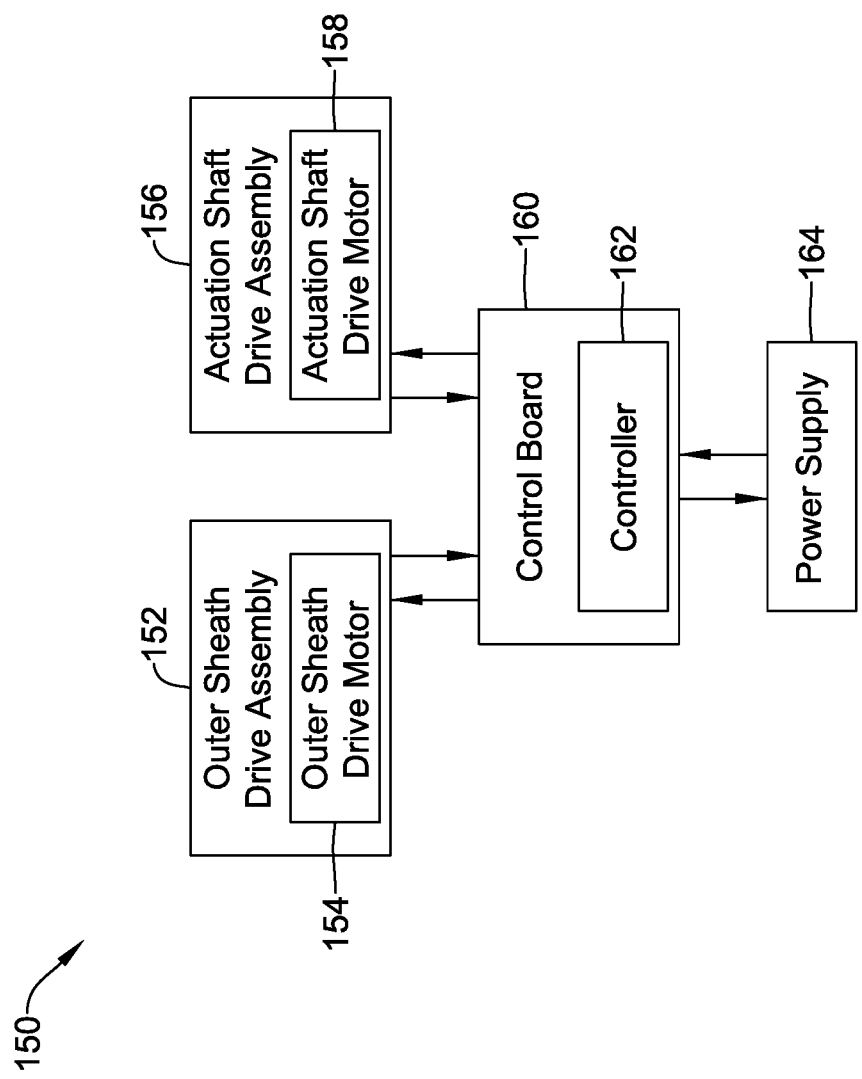
FIG. 10 is a schematic block diagram of an example medical device delivery system.

FIG. 10 shows a system 150 that may be considered as being representative of the medical device system 10, and may for example be manifested within the handle 17. The system 150 has an outer sheath drive assembly 152 including an outer sheath drive motor 154. The system 150 has an actuation shaft drive assembly 156 including an actuation shaft drive motor 158. It will be appreciated that the outer sheath drive assembly 152 may be considered as representing the outer sheath drive assembly 74 shown in FIG. 7 and the actuation shaft drive assembly 156 may be considered as representing the actuation shaft drive assembly 76 shown in FIG. 8.

A control board 160 includes a controller 162. In some cases, the controller 162 may be configured to control operation of the outer sheath drive assembly 152 (including the outer sheath drive motor 154) and/or the actuation shaft drive assembly 156 (including the actuation shaft drive motor 158). In some cases, the controller 162 may receive feedback from the outer sheath drive assembly 152 and/or the actuation shaft drive assembly 156 and may utilize such feedback in controlling the outer sheath drive assembly 152 and/or the actuation shaft drive assembly 156. In some cases, a power supply 164 may be disposed within the handle 17 and may be operably coupled to the controller 162.

The materials that can be used for the various components of the medical devices and/or system 10 disclosed herein may include those commonly associated with medical devices. However, this is not intended to limit the devices and methods described herein, as the discussion may be applied to other components of the medical devices and/or systems 10 disclosed herein including the various shafts, liners, components described relative thereto.

The medical device 10 may be made from a metal, metal alloy, polymer (some examples of which are disclosed below), a metal-polymer composite, ceramics, combinations thereof, and the like, or other suitable material. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), high density polyethylene (HDPE), polyester, Marlex high-density polyethylene, Marlex low-density polyethylene, linear low density polyethylene (for example REXELL®), ultra-high molecular weight (UHMW) polyethylene, polypropylene, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like. In some embodiments the sheath can be blended with a liquid crystal polymer (LCP).

Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

In at least some embodiments, portions or all of the medical device 10 may also be doped with, made of, or otherwise include a radiopaque material. Radiopaque materials are understood to be materials capable of producing a relatively bright image on a fluoroscopy screen or another imaging technique during a medical procedure. This relatively bright image aids the user of the medical device 10 in determining its location. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of the medical device 10 to achieve the same result.

In some embodiments, a degree of Magnetic Resonance Imaging (MM) compatibility is imparted into the medical device 10. For example, the medical device 10 may include a material that does not substantially distort the image and create substantial artifacts (e.g., gaps in the image). Certain ferromagnetic materials, for example, may not be suitable because they may create artifacts in an MRI image. The medical device 10 may also be made from a material that the MM machine can image. Some materials that exhibit these characteristics include, for example, tungsten, cobalt-chromium-molybdenum alloys (e.g., UNS: R30003 such as ELGILOY®, PHYNOX®, and the like), nickel-cobalt-chromium-molybdenum alloys (e.g., UNS: R30035 such as MP35-N® and the like), nitinol, and the like, and others.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The disclosure's scope is, of course, defined in the language in which the appended claims are expressed.

What is claimed is:

1. A system for delivering an implantable medical device, comprising:
    a handle housing;
    an outer sheath coupler secured to a proximal end of an outer sheath, the outer sheath configured to cover at least a portion of the implantable medical device;
    an outer sheath drive assembly operably coupled to the outer sheath coupler, the outer sheath drive assembly configured to translate the outer sheath relative to the handle housing;
    an actuation shaft coupler secured to a proximal end of an actuation shaft, the actuation shaft extending within the outer sheath; and
    an actuation shaft drive assembly operably coupled to the actuation shaft coupler, the actuation shaft drive assembly configured to cause the actuation shaft to translate relative to the handle housing and shift the implantable medical device between a first position and a second position in which the implantable medical device is radially expanded relative to the first position;
    an outer sheath drive assembly motor having a motor coupling; and
    an outer sheath drive assembly threaded rod operably coupled to the motor coupling such that actuation of the outer sheath drive assembly motor causes the outer sheath drive assembly threaded rod to rotate,
    wherein the outer sheath drive assembly comprises a thrust bearing configured to secure the outer sheath drive assembly threaded rod at an end away from the outer sheath drive assembly motor while permitting the outer sheath drive assembly threaded rod to rotate relative to the thrust bearing.

2. The system of claim 1, wherein the outer sheath drive assembly comprises:
    an outer sheath nut threadedly engaged with the outer sheath drive assembly threaded rod and held against rotation such that rotation of the outer sheath drive assembly threaded rod causes the outer sheath nut to translate relative to the outer sheath drive assembly threaded rod;
    wherein the outer sheath nut is configured to engage the outer sheath coupler such that translation of the outer sheath nut relative to the outer sheath drive assembly threaded rod causes the outer sheath to translate relative to the handle housing.

3. The system of claim 2, wherein the outer sheath nut is held against rotation by virtue of being engaged with the outer sheath coupler.

4. The system of claim 2, wherein the outer sheath drive assembly motor comprises a direct drive motor.

5. The system of claim 2, wherein the outer sheath drive assembly motor further comprises a gearbox.

6. The system of claim 1, wherein the actuation shaft drive assembly comprises:
    an actuation shaft drive assembly motor having a motor coupling;
    an actuation shaft drive assembly threaded rod operably coupled to the motor coupling of the actuation shaft drive assembly motor such that actuation of the actuation shaft drive assembly motor causes the actuation shaft drive assembly threaded rod to rotate; and
    an actuation shaft nut threadedly engaged with the actuation shaft drive assembly threaded rod and held against rotation such that rotation of the actuation shaft drive assembly threaded rod causes the outer sheath nut to translate relative to the actuation shaft drive assembly threaded rod;
    wherein the actuation shaft nut is configured to engage the actuation shaft coupler such that translation of the actuation shaft nut relative to the actuation shaft drive assembly threaded rod causes the outer sheath to translate relative to the handle housing.

7. The system of claim 6, wherein the actuation shaft drive assembly further comprises a thrust bearing configured to secure the actuation shaft drive assembly threaded rod at an end away from the actuation shaft drive assembly motor while permitting the actuation shaft drive assembly threaded rod to rotate relative to the thrust bearing of the actuation shaft drive assembly.

8. The system of claim 6, wherein the actuation shaft drive nut is held against rotation by virtue of being engaged with the activation shaft coupler.

9. The system of claim 1, wherein the actuation shaft coupler is disposed within the handle housing at a position that is proximal of the outer sheath coupler.

10. The system of claim 1, further comprising a controller disposed within the handle housing and configured to control operation of the outer sheath drive assembly and/or the actuation shaft drive assembly.

11. The system of claim 10, wherein the controller is further configured to receive feedback from the outer sheath drive assembly and/or the activation shaft drive assembly.

12. The system of claim 10, further comprising a power supply disposed within the handle housing and operably coupled to the controller.

13. A system for delivering an implantable medical device, comprising:
    a handle housing;
    an outer sheath configured to cover at least a portion of the implantable medical device;
    an outer sheath coupler secured to the outer sheath such that translation of the outer sheath coupler relative to the handle housing causes translation of the outer sheath relative to the handle housing;
    an outer sheath nut threadedly disposed on a first threaded rod and operably coupled to the outer sheath coupler;
    an outer sheath drive motor operably coupled to the outer sheath nut such that actuation of the outer sheath drive motor causes the outer sheath nut to translate relative to the first threaded rod and thus causes the outer sheath coupler to translate relative to the handle housing;
    an actuation shaft extending within the outer sheath and operably coupled to translation members secured relative to the implantable medical device such that translation of the actuation shaft causes translation of the translation members which in turn causes the implantable medical device to shift from a delivery configuration to a deployment configuration;
    an actuation shaft coupler secured to the actuation shaft such that translation of the actuation shaft coupler relative to the handle housing causes translation of the actuation shaft relative to the handle housing;
an actuation shaft nut threadedly disposed on a second threaded rod and operably coupled to the actuation shaft coupler;
an actuation shaft drive motor operably coupled to the actuation shaft nut such that actuation of the actuation shaft drive motor causes the actuation shaft nut to translate relative to the second threaded rod and thus causes the actuation shaft coupler to translate relative to the handle housing; and
a first thrust bearing configured to secure the first threaded rod at an end away from the outer sheath drive motor while permitting the first threaded rod to rotate relative to the first thrust bearing.

14. The system of claim 13, further comprising a second thrust bearing configured to secure the second threaded rod at an end away from the activation shaft drive motor while permitting the second threaded rod to rotate relative to the second thrust bearing.

15. The system of claim 13, wherein the outer sheath nut has an overall length of about 12 mm to about 150 mm.

16. The system of claim 13, wherein the actuation shaft nut has an overall length of about 12 mm to about 150 mm.

17. The system of claim 13, further comprising a controller disposed within the handle housing and configured to control operation of the outer sheath drive motor and/or the actuation shaft drive motor.

18. A system for delivering an implantable medical device, comprising:
a handle housing;
an actuation shaft operably coupled to translation members secured relative to the implantable medical device such that translation of the actuation shaft causes translation of the translation members which in turn causes the implantable medical device to shift from a delivery configuration to a deployment configuration;
an actuation shaft coupler secured to the activation shaft such that translation of the actuation shaft coupler relative to the handle housing causes translation of the actuation shaft relative to the handle housing;
an actuation shaft nut threadedly disposed on a threaded rod and operably coupled to the actuation shaft coupler;
an actuation shaft drive motor operably coupled to the actuation shaft nut such that actuation of the actuation shaft drive motor causes the actuation shaft nut to translate relative to a second threaded rod and thus causes the actuation shaft coupler to translate relative to the handle housing; and
a thrust bearing configured to secure the threaded rod at an end away from the actuation shaft drive motor while permitting the threaded rod to rotate relative to the thrust bearing.

\* \* \* \* \*